US00PP16054P2

(12) United States Plant Patent
Korlipara

(10) Patent No.: US PP16,054 P2
(45) Date of Patent: Oct. 18, 2005

(54) ***ECHINACEA PURPUREA* PLANT NAMED 'FRAGRANT ANGEL'**

(50) Latin Name: *Echinacea purpurea*
Varietal Denomination: Fragrant Angel

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 39 days.

(21) Appl. No.: 10/871,829

(22) Filed: Jun. 18, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Echinacea purpurea* plant named 'Fragrant Angel' characterized by its unique flowers with clean white rays that are spread out perpendicular to the stem, orange cone, lovely fragrance, and an upright vigorous habit.

1 Drawing Sheet

Botanical name: *Echinacea purpurea.*
Variety designation: 'Fragrant Angel'.

The present invention relates to a new and distinct cultivar of *Echinacea purpurea* and given the cultivar name 'Fragrant Angel'. *Echinacea* is in the family Asteraceae. This new cultivar originated as a crown section mutation in a mass planting of *Echinacea purpurea* 'Ruby Giant' (an unpatented plant) in the nursery trial fields in Canby, Oreg.

This new *Echinacea purpurea* cultivar is distinguished by:

1. Large white flowers with a double row of rays flowers.
2. Lovely fragrance.
3. Ray flowers spread out stiffly, parallel to ground.
4. Strong upright stems.
5. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two year old *Echinacea purpurea* 'Fragrant Angel' growing in the ground in the field in the summer in Canby, Oreg.

DETAILED PLANT DESCRIPTION

The following is a detailed description of the new *Echinacea purpurea* cultivar based on observations of a one-year-old specimen growing in the trial fields in Canby, Oreg. The color descriptions are all based on The Royal Horticultural Society Colour Chart.

Botanical name: *Echinacea purpurea.*
Variety designation: 'Fragrant Angel'.

Plant:
- *Type.*—Herbaceous perennial.
- *Hardiness.*—USDA Zones 4 to 9.
- *Size.*—30 cm wide and 78 cm. tall to top of flowers.
- *Form.*—Basal clump.

Leaf:
- *Type.*—Simple.
- *Shape.*—Ovate.
- *Arrangement.*—Alternate.
- *Blade length.*—8 to 15 cm.
- *Width.*—4.5 to 7 cm. at the widest part.
- *Margins.*—Serrate.
- *Apex.*—Acuminate.
- *Base.*—Attenuate, continuing down petiole.
- *Texture.*—Like sandpaper.
- *Vestiture.*—Strigose.
- *Venation.*—Pinnate, with three main veins from near the base.
- *Color.*—Topside — Deep Green, Yellow Green 147A. Bottom — Yellow Green 147B.
- *Petiole length.*—16.5 cm if basal leaf, 1 to 1.5 cm if cauline leaf.
- *Petiole vestiture.*—Strigose.
- *Petiole color.*—Yellow Green 146C.

Inflorescence:
- *Type.*—Long stalked terminal heads.
- *Peduncle.*—Strong and fibrous, makes a good cut flower. Height: 78 cm. Diameter: 0.9 cm. near flower head. Vestiture: Strigose. Color: Yellow Green 146C speckled with Yellow Green 145C.
- *Number of blooms.*—9 to 15 over the season (as the crown matures the number of blooms increases).

Flower:
- *Type.*—Perfect, zygomorphic.
- *Size.*—12.5 cm. wide and 2 to 5 cm deep as disc enlarges.

*Immature inflorescence.*—While still developing the ray petals are upright and Yellow Green 145D. The disc flowers are Yellow Green 144A. Disc size ranges from 3 cm to 3.7 cm wide.

*Ray petals.*—In 2 series so there is little or no space between petals, average number is 32. Shape: Oblanceolate with the tip two toothed. Size: 5.7 cm long, 1.3 cm wide. Texture — Satiny, soft. Vestiture — Glabrous and strigose on bottom on main veins.

*Disc.*—Average number of disc florets between 345 and 400. Shape — Convex becoming conic. Size — 4.5 to 4.8 cm wide and becoming 3.5 cm deep with maturity. Flower — 1.1 cm long, Yellow Green 146D, 5 lobed, each flower with one persistent, very stiff bract, 1.5 cm long, which gives the orange disc color. Pistil — 1 per floret, in both ray and disc florets, 0.6 cm long, extruding, stigma, style and ovary all Yellow Green 145C, a 2-branched stigma. Stamen — 5 in number, in both ray and disc florets, 4 mm long, Yellow Green 145C, with anthers oval, 0.1 mm long. Pollen color — Yellow Orange 19A.

*Color.*—Ray, topside — White 155B. Ray, bottom side — Yellow White 158D with Yellow Green 146A at both ends. Disc — Orange Group 24A.

*Bracts* (*at the base of each head*).—Involucral bracts in six leafy series, lobes lanceolate in shape, reflexed, strigose, area 3.5 to 5 cm wide.

*Bract size.*—Range from 5 to 9 mm deep and 3 to 5 mm wide.

*Bract color.*—Yellow Green 146A.

*Bloom period.*—July through September in Canby, Oreg.

*Fragrance.*—Lovely, strong.

*Lastingness.*—Each flower head lasts two to three weeks on the plant.

Fruit: Achene.

Seed: Average 100 seeds/head.

*Description.*—4.5 mm long and 2 mm wide, oval, tan, Grey Brown 199D.

*Fertility.*—Good.

Disease and pests: *Echinacea* are susceptible to leaf miners, powdery mildew, bacterial spots, and gray mold. None of these have been observed on plants grown under commercial conditions in Canby, Oreg.

COMPARISONS TO SIMILAR *Echinacea*

Compared to *Echinacea purpurea* 'Ruby Giant', an unpatented plant, the flowers of this new cultivar are white instead of red purple in color. The overall plant is lighter colored, without dark peduncles.

Compared to *Echinacea purpurea* 'White Swan', an unpatented seed strain, the new cultivar has ray petals in two series rather than one, with the ray petals stiffly parallel to the ground rather than weeping or variable, and a disc that is orange rather than gold brown.

Compared to *Echinacea purpurea* 'Kim's Mop Head' (U.S. Plant Pat. No. 13,560), the new cultivar is taller with the flowers with ray petals stiffly parallel to the ground rather than weeping, and with the disc orange rather than greenish. Also the ray petals of the new cultivar are white rather than cream.

Compared to *Echinacea purpurea* 'Cygnet White', an unpatented plant, the new cultivar has ray petals in two series rather than one, with the ray petals stiffly parallel to the ground rather than slightly weeping, and it is taller.

I claim:

1. A new and distinct cultivar of *Echinacea purpurea* plant named 'Fragrant Angel' as illustrated and described.

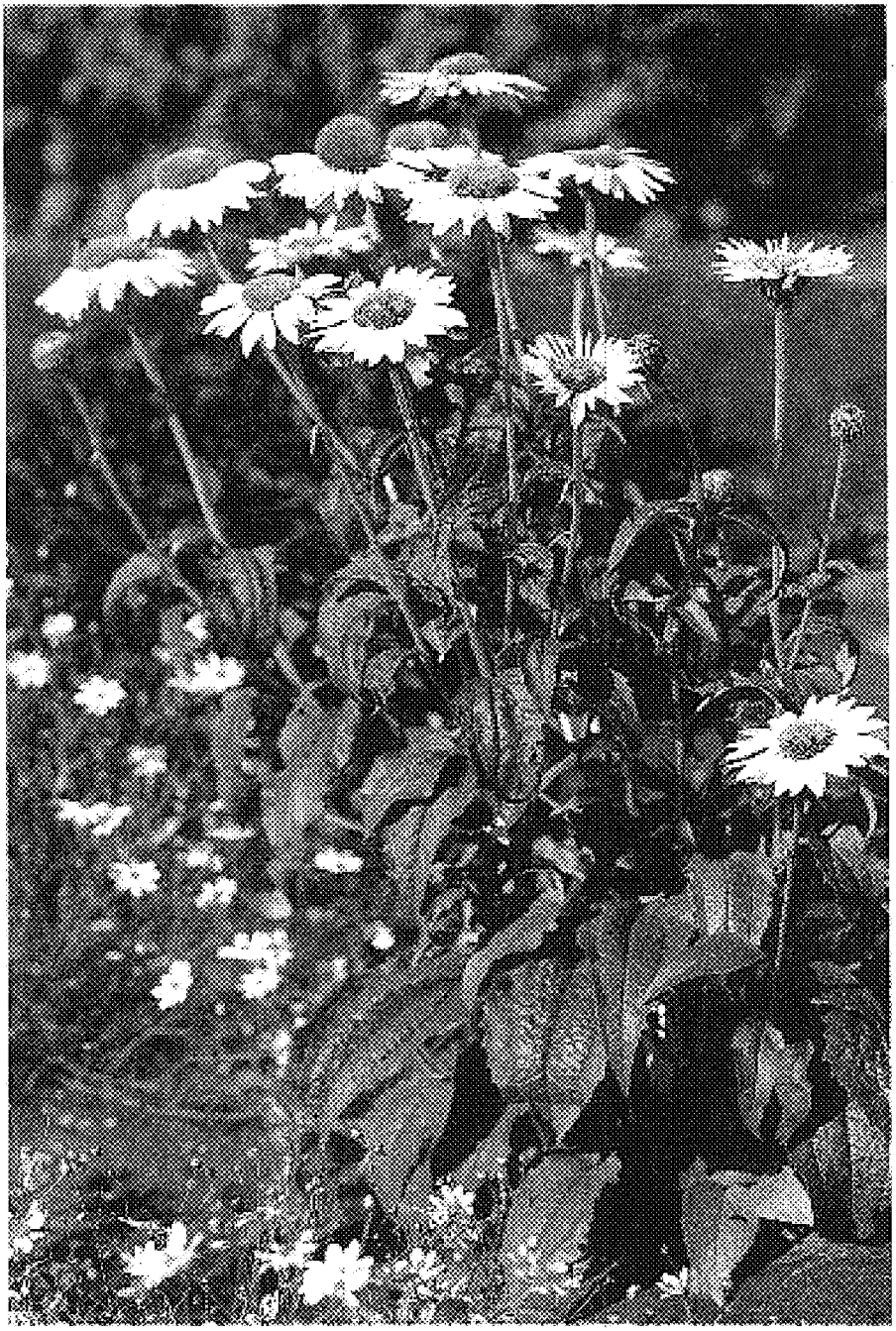

* * * * *